(12) United States Patent
Gerber et al.

(10) Patent No.: US 7,328,070 B2
(45) Date of Patent: Feb. 5, 2008

(54) MULTI-TUBE SENSOR FOR SENSING URINARY SPHINCTER AND URETHRAL PRESSURE

(75) Inventors: Martin T. Gerber, Maple Grove, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/117,079

(22) Filed: Apr. 28, 2005

(65) Prior Publication Data

US 2006/0247725 A1    Nov. 2, 2006

(51) Int. Cl.
*A61N 1/00* (2006.01)
*A61B 5/00* (2006.01)
*A61B 5/103* (2006.01)
*A61B 5/117* (2006.01)

(52) U.S. Cl. .................. 607/41; 600/561; 600/587
(58) Field of Classification Search ............. 600/561, 600/587, 29, 30; 607/39–41
See application file for complete search history.

(56) References Cited

U.S. PATENT DOCUMENTS

| | | | |
|---|---|---|---|
| 4,846,191 A * | 7/1989 | Brockway et al. ........ | 600/561 |
| RE33,360 E * | 10/1990 | Reynolds et al. ......... | 600/488 |
| 5,103,835 A | 4/1992 | Yamada et al. | |
| 5,134,281 A | 7/1992 | Bryenton et al. | |
| 5,207,648 A * | 5/1993 | Gross .................. | 604/164.09 |
| 5,396,897 A * | 3/1995 | Jain et al. .............. | 600/561 |
| 5,554,139 A * | 9/1996 | Okajima ................ | 604/526 |
| 5,573,007 A * | 11/1996 | Bobo, Sr. .............. | 600/561 |
| 6,015,393 A | 1/2000 | Hovland et al. | |
| 6,162,188 A | 12/2000 | Barnea | |
| 6,354,991 B1 | 3/2002 | Gross et al. | |

(Continued)

FOREIGN PATENT DOCUMENTS

EP    0694284 A1 *    1/1996

OTHER PUBLICATIONS

Coosemans et al., "Datalogger for Bladder Pressure Monitoring with Wireless Power and Data Transmission," Katholieke Universiteit Leuven, Department ESAT-MICAS, Belgium, 1 pg. (Oct. 17, 2003).

(Continued)

*Primary Examiner*—Max F. Hindenburg
*Assistant Examiner*—Michael Apanius
(74) *Attorney, Agent, or Firm*—Shumaker & Sieffert, P.A.

(57) ABSTRACT

The disclosure describes a multi-tube pressure sensor to measure the pressure at two sites that may be used in a therapeutic incontinence control system. The system senses urinary sphincter pressure and urethral pressure and sends the information to a stimulator that is capable of stimulation therapy to control sphincter contractility, thus reducing unwanted urinary incontinence. Measuring sphincter pressure is accomplished through the use of a tube placed through the sphincter and urethral pressure is measured by a second tube placed within the urethra, both tubes may be attached to a single module implanted within the bladder. Pressure within the tube generates an electrical signal that is sent wirelessly to an implanted stimulator connected to a lead positioned near pelvic floor nerves. An external device may be used to wirelessly send information to the implanted stimulator and inhibit stimulation in order for the patient to empty the bladder. Additionally, the pressure information and stimulation information may be recorded and reviewed for continued patient monitoring.

28 Claims, 10 Drawing Sheets

U.S. PATENT DOCUMENTS

| | | |
|---|---|---|
| 6,360,123 B1 | 3/2002 | Kimchi et al. |
| 6,393,323 B1 | 5/2002 | Sawan et al. |
| 6,650,943 B1 | 11/2003 | Whitehurst et al. |
| 6,652,449 B1 | 11/2003 | Gross et al. |
| 6,689,056 B1 | 2/2004 | Kilcoyne et al. |
| 2002/0055761 A1* | 5/2002 | Mann et al. ............ 607/41 |
| 2002/0062060 A1 | 5/2002 | Gross et al. |
| 2002/0103424 A1 | 8/2002 | Swoyer et al. |
| 2002/0111586 A1* | 8/2002 | Mosel et al. ............ 604/174 |
| 2003/0100930 A1* | 5/2003 | Cohen et al. ............ 607/40 |
| 2003/0220292 A1 | 11/2003 | Okada et al. |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0147871 A1* | 7/2004 | Burnett ............ 604/9 |
| 2004/0152999 A1* | 8/2004 | Cohen et al. ............ 600/561 |
| 2005/0065408 A1* | 3/2005 | Benderev ............ 600/202 |
| 2005/0177067 A1* | 8/2005 | Tracey et al. ............ 600/561 |
| 2005/0245840 A1* | 11/2005 | Christopherson et al. ... 600/561 |
| 2005/0288603 A1* | 12/2005 | Goping ............ 600/561 |

OTHER PUBLICATIONS

Siwapornsathain et al., "A Telemetry and Sensor Platform for Ambulatory Urodynamics," Department of Electrical and Computer Engineering, University of Wisconsin, Madison, WI, 5 pgs. (2002).

Van Waalwijk van Doorn, "Standarisation of Ambulaatory Urodynamic Monitoring," Report of the Standarisation Sub-committee of the ICS ambulatory urodynamic studies, 21 pgs. (2000).

"Wireless Physiological Pressure Transducer," MEMSCAP Sensor-Solutions, 2 pgs. (May 2003).

U.S. Patent Application entitled "Implantable Optical Pressure Sensor for Sensing Urinary Sphincter Pressure", U.S. Appl. No. 11/117,064, filed on Apr. 28, 2005.

U.S. Patent Application entitled "Tube Sensor for Penile Tumescence", U.S. Appl. No. 11/117,054, filed on Apr. 28, 2005.

U.S. Patent Application entitled "Flexible Tube Sensor for Sensing Urinary Sphincter Pressure", U.S. Appl. No. 11/116,952, filed on Apr. 28, 2005.

* cited by examiner

MULTI-TUBE SENSOR FOR SENSING URINARY SPHINCTER AND URETHRAL PRESSURE

TECHNICAL FIELD

The invention relates to implantable medical devices and, more particularly, implantable sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Electrical stimulation of nerves in the pelvic floor may provide an effective therapy for a variety of disorders, including urinary incontinence. For example, an implantable neurostimulator may be provided to deliver electrical stimulation to the sacral nerve to induce sphincter constriction and thereby close or maintain closure of the urethra at the bladder neck. An appropriate course of neurostimulation therapy may be aided by a sensor that monitors physiological conditions with the urinary tract. In some cases, an implantable stimulation device may deliver stimulation therapy based on the level or state of a sensed physiological condition.

SUMMARY

The invention is directed to a sensor that is implantable to sense urinary sphincter pressure and urethral pressure using two or more flexible tubes, as well as a neurostimulation system and method that make use of such a sensor for alleviation of urinary incontinence. The sensor includes two or more thin, flexible tubes, each coupled to a sensing element to detect pressure levels within the respective tube.

Each flexible tube may contain a volume of fluid and a sensing element, such as a strain gauge sensor, to detect changes in the pressure of the fluid as the urinary sphincter, urethra, or flow within the urethra exerts pressure against the tube. As an alternative, each flexible tube may include an optical fiber pressure sensor that detects pressure based on one or more properties of light transmitted and received via the optical fiber as the urinary sphincter, urethra, or flow within the urethra exerts pressure against the tube.

In each case, flexible tubes are deployed within the bladder neck and urethra to transduce pressure exerted by the urinary sphincter, urethra, or urethral flow as a function of the pressure within the flexible tube. The ability to monitor pressure within the urinary sphincter and urethra simultaneously may prove useful in diagnosing and devising therapies for treatment of urinary incontinence, as well as closed loop feedback for adjustment of neurostimulation therapies in response to pressure changes.

Inadequate sphincter pressure may result in involuntary bladder voiding, i.e., incontinence. The sensor may provide short- or long-term monitoring of urinary sphincter and urethra pressure, e.g., for analysis by a clinician. Alternatively, a sensor using flexible tubes may form part of a closed-loop neurostimulation system. For example, neurostimulation therapy can be applied to increase sphincter pressure, and thereby prevent involuntary urine leakage. In particular, an implantable neurostimulator may be responsive to urinary sphincter and urethral pressure signals generated by a sensor, as described herein, to provide closed loop neurostimulation therapy to alleviate incontinence.

In one embodiment, the invention provides an implantable pressure sensor comprising a sensor housing, a first flexible tube extending from the housing, a second flexible tube extending from the housing, a sensing device that senses a fluid pressure within the first flexible tube indicative of a urinary sphincter pressure level when the first flexible tube is positioned adjacent a urinary sphincter of a patient, and senses a fluid pressure within the second flexible tube indicative of a urethral pressure level when the second flexible tube is positioned within a urethra of the patient.

In another embodiment, the invention comprises a system comprising and implantable pressure sensor and an implantable stimulator. The implantable pressure sensor comprises a sensor housing, a first flexible tube extending from the housing, a second flexible tube extending from the housing, and a sensing device that senses a fluid pressure within the first flexible tube indicative of a urinary sphincter pressure level when the first flexible tube is positioned adjacent a urinary sphincter of a patient, and senses a fluid pressure within the second flexible tube indicative of a urethral pressure level when the second flexible tube is positioned within a urethra of the patient. The implantable stimulator delivers electrical stimulation to the patient based on the sensed pressures.

In an additional embodiment, the invention provides a method comprising sensing a first pressure level exerted by a urinary sphincter within a patient based on a pressure of fluid within a first flexible tube placed proximate to the urinary sphincter, and sensing a second pressure level exerted within a urethra of the patient based on a pressure of fluid within a second flexible tube placed within the urethra below the urinary sphincter.

Although the invention may be useful in sensing urinary sphincter pressure, the invention alternatively may be applied more generally to other sphincters and adjacent structures within the patient, such locations including the lower esophageal sphincter (LES) or pyloric sphincter. In addition, the invention may be adapted in those cases to support electrical stimulation of those sphincters or other body organs, such as the stomach or intestines, e.g., for treatment of obesity or gastric mobility disorders.

Various embodiments of the invention may provide one or more advantages. For example, the use of thin and flexible tube sensors permits pressure to be sensed within the narrow, constricted passage proximate the urinary sphincter and urethra. In this manner, pressure can be sensed without significantly obstructing or altering the physiological function of the urinary tract.

The flexible tube sensor may be coupled to a larger sensor housing that resides within the bladder and houses sensor electronics for measuring the pressure level on the tubes. The sensor permits pressure information to be obtained on a continuous or periodic basis as the patient goes about a daily routine. Also, the flexible nature of each tube permits the sensor to be implanted in a variety of locations, and to be constructed in variety of shapes and sizes.

The flexible tube sensor may transmit sensed pressure information to an implantable stimulator to enable dynamic control of the therapy delivered by the stimulator on a closed-loop basis. For example, the stimulator may adjust certain stimulation parameters, such as amplitude, pulse width or pulse rate, in response to the sensed pressures. In this manner, the stimulator can provide enhanced efficacy and prevent involuntary leakage. In addition, or alternatively, adjustment may involve on and off cycling of the stimulation in response to pressure levels indicative of a particular bladder fill stage. For example, stimulation may be turned off until the pressure level exceeds a threshold indicative of a particular fill stage of the bladder.

In addition, closed-loop stimulation may allow the stimulator to generate stimulation parameter adjustments that more effectively target the function of the urinary sphincter muscle, thereby enhancing stimulation efficacy. In some patients, more effective stimulation via the sacral nerve may actually serve to strengthen the sphincter muscle, restoring proper operation and eliminating the need to interventional therapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
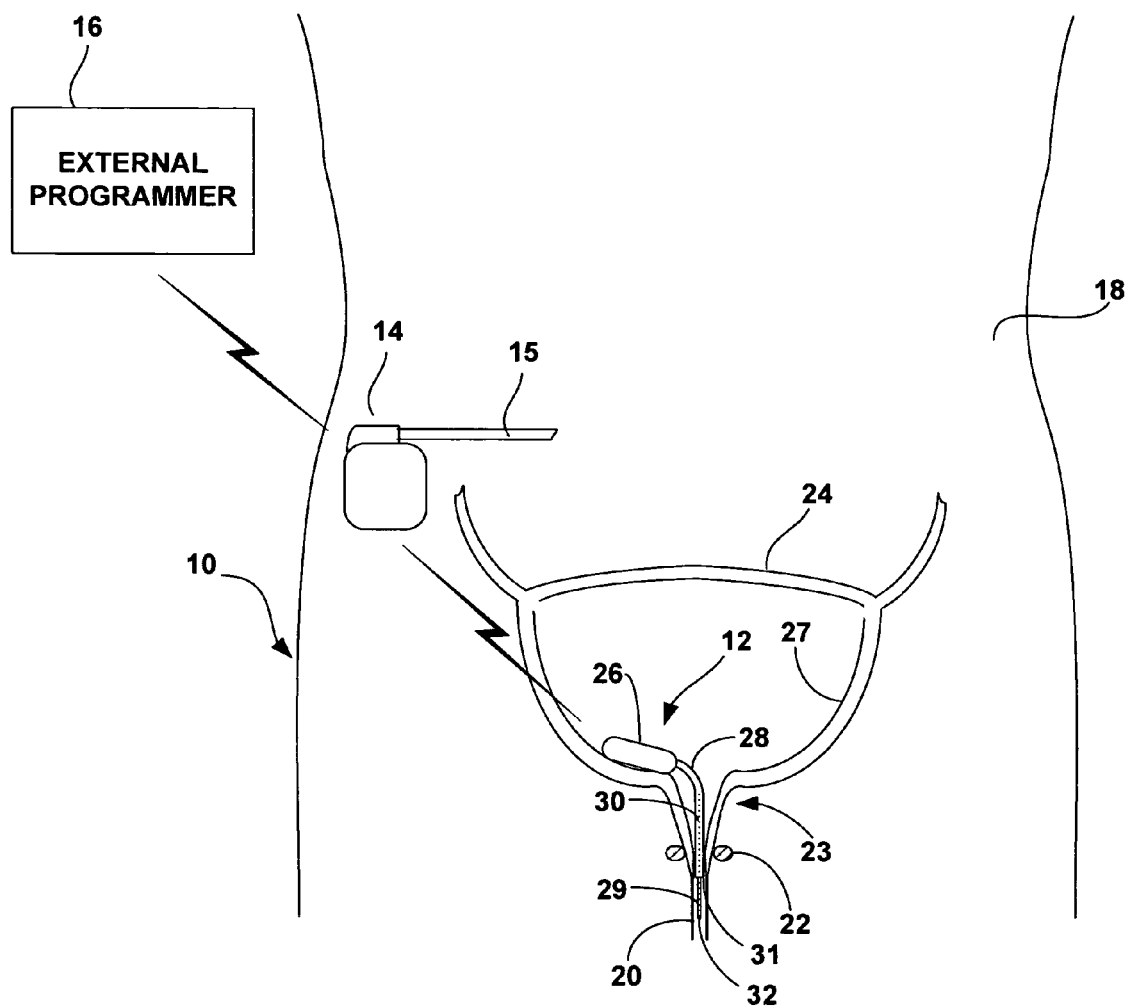
FIG. 1 is a schematic diagram illustrating an implantable stimulation system, incorporating a sensor detecting urinary sphincter and urethra pressure, for alleviation of urinary incontinence.

FIG. 1 is a schematic diagram illustrating an implantable stimulation system 10 for alleviation of urinary incontinence. As shown in FIG. 1, system 10 may include an implantable pressure sensor 12, implantable stimulator 14 and external programmer 16 shown in conjunction with a patient 18. Pressure sensor 12 senses a pressure level exerted by urinary sphincter 22 and urethra 20 adjacent to neck 23 of bladder 24, and transmits pressure information based on the multiple sensed pressure levels to stimulator 14, programmer 16 or both, by wireless telemetry. Stimulator 14 or programmer 16 may record the information, generate adjustments to electrical stimulation parameters applied by the stimulator, or both.

Figure 2:
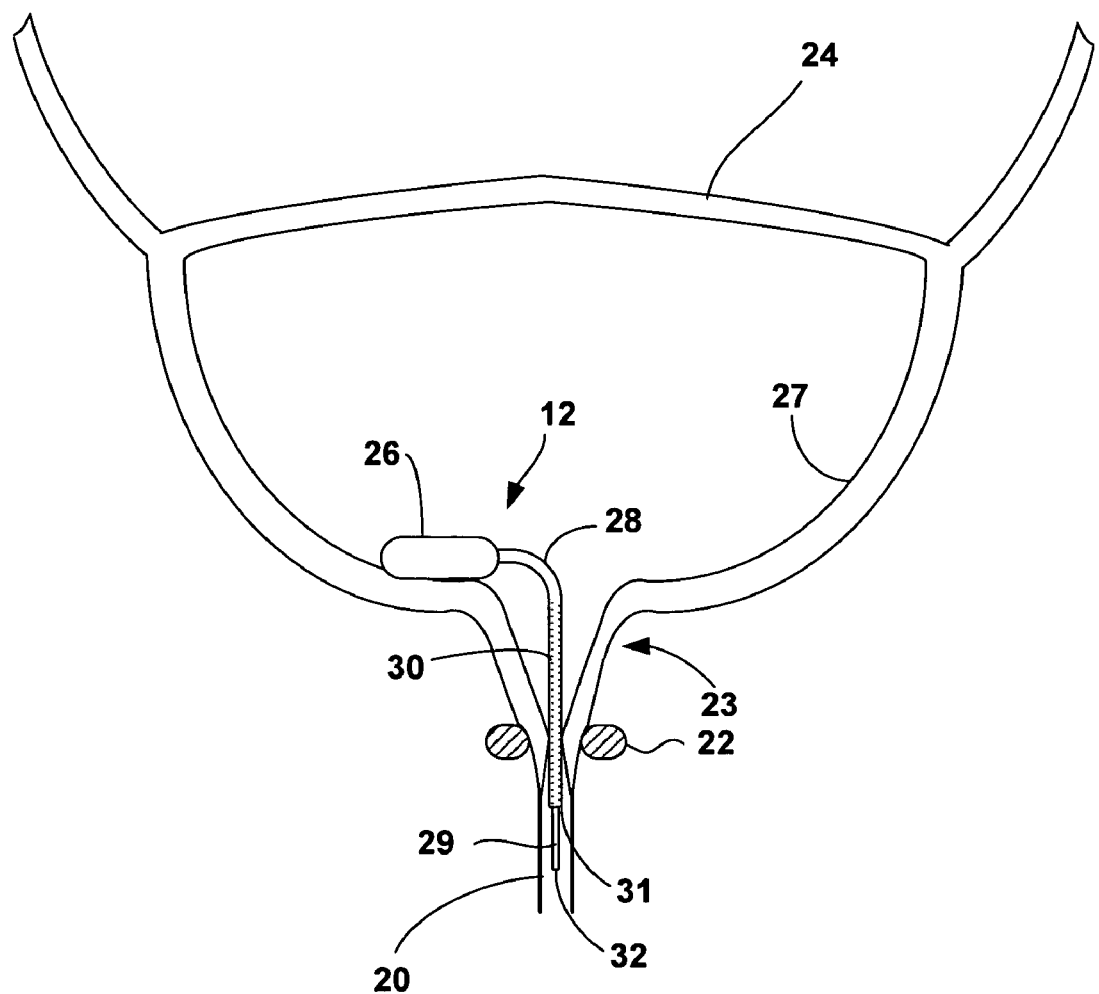
FIG. 2 is an enlarged schematic diagram illustrating an implantable pressure sensor with two flexible tubes extending through the urinary sphincter of a patient.

FIG. 2 is an enlarged schematic diagram illustrating implantable pressure sensor 12. As shown in FIGS. 1 and 2, pressure sensor 12 includes a sensor housing 26 and flexible tubes 28 and 29 that extend from the housing. In the example of FIGS. 1 and 2, a flexible, inner tube 29 resides concentrically within a flexible, outer tube 28. Hence, the cross-section of inner tube 29 is substantially circular, while the cross-section of outer tube 28 is substantially annular. The outer surface of outer tube 28 is preferably cylindrical, providing a surface that promotes sealing of urinary sphincter 22 about outer tube 28 to prevent leakage when urinary sphincter is closed.

Closed end 31 seals tube 28 and closed end 32 seals tube 29. Each tube 28, 29 includes an open end proximal to sensor housing 26. Sensor housing 26 contains sensing elements(not shown in FIG. 1), one for each tube 28, 29, adjacent the open ends of the tubes. The sensing elements sense the pressure within each flexible tube 28, 29. The pressure within outer tube 28 provides an indication of the pressure level exerted by urinary sphincter 22. The inner tube 29 extends further downward into urethra 20. The pressure within inner tube 29 provides an indication of the pressure level exerted within urethra 20, e.g., by urine flow. Sensor housing 26 further contains electronics to generate pressure information, and telemetry circuitry for transmission of the information to stimulator 14, programmer 16 or both.

As further shown in FIGS. 1 and 2, sensor housing 26 may reside within bladder 24. Sensor housing 26 may be temporarily or permanently attached to an inner wall 27 of bladder 24, such as the mucosal lining, as will be described. Alternatively, housing 26 may be implanted sub-mucosally. Flexible tubes 28 and 29 extend away from sensor housing 26 and through an inner lumen defined by the bladder neck proximate urinary sphincter 22. In this manner, flexible tube 28 is positioned to sense the pressure level exerted by urinary sphincter 22. Flexible tube 29 extends further downstream to measure the pressure level within urethra 20. Yet, both flexible tubes 28 and 29 may be sufficiently thin to avoid significant obstruction of urethra 20 or disruption of the function of urinary sphincter 22.

As a further alternative, housing 26 may reside outside bladder 24, in which case flexible tubes 28, 29 may extend into bladder 24 and through urinary sphincter 22 through a hole formed in the bladder. In this case, housing 26 may be surgically or laparoscopically implanted within the abdomen. Tubes 28, 29 may be surgically or laparoscopically guided through a hole in the wall of bladder 24. A cystoscope may be used to grab tubes 28, 29 and pull them downward through urinary sphincter 22 and urethra 20. In some embodiments, housing 26 and its contents may be integrated with stimulator 14, in which case flexible tubes 28, 29 extend from the stimulator housing and into bladder 24, much like leads carrying stimulation or sense electrodes.

As a further alternative, housing 26 may reside outside bladder 24, in which case flexible tubes 28, 29 may extend into bladder 24 and through urinary sphincter 22 through a hole formed in the bladder. In this case, housing 26 may be surgically or laparoscopically implanted within the abdomen. Tube 28 may be surgically or laparoscopically guided through a hole in the wall of bladder 24. A cystoscope may be used to grab tube 28 and pull them downward through urinary sphincter 22 and urethra 20. In some embodiments, housing 26 and its contents may be integrated with stimulator 14, in which case flexible tube 28 extends from the stimulator housing and into bladder 24, much like leads carrying stimulation or sense electrodes.

With further reference to FIG. 1, implantable stimulator 14 includes an electrical lead 15 (partially shown in FIG. 1) carrying one or more electrodes that are placed at a nerve site within the pelvic floor. For example, the electrodes may be positioned to stimulate the sacral nerve or pudendal nerve and thereby innervate urinary sphincter 22. In particular, electrical stimulation may be applied to cause urinary sphincter 22 to increase closing pressure to avoid involuntary leakage from bladder 24. Alternatively, if voluntary voiding is desired by patient 18, electrical stimulation may be suspended or reduced to lessen the closing pressure exerted by urinary sphincter 22 on urethra 20 at the bladder neck.

For spinal cord injury patients who cannot perceive a sensation of bladder fullness, sphincter pressure sensed by pressure sensor 12 may be transmitted to external programmer 16, with or without an accompanying stimulator 14, to advise the patient when urinary sphincter pressure is high, indicating bladder fullness. In this case, the advice may be in the form of a audible, visual or vibratory stimulus. In response to the advice, the spinal cord injury patient is able to catheterize the urethra 20 and bladder 24 to voluntarily relieve urine.

Implantable stimulator 14 delivers stimulation therapy to the sacral nerve in order to keep the sphincter 22 constricted and keep contents of bladder 24 from leaking out through urethra 20. At predetermined times, or at patient controlled instances, the external programmer 16 may program stimulator 14 to interrupt the stimulation to allow the sphincter to relax, thus permitting voiding of bladder 24. Upon completion of the voiding event, external programmer 16 may program stimulator 14 to resume stimulation therapy and thereby maintain closure of urinary sphincter 22.

In addition, adjustment of stimulation parameters may be responsive to pressure information transmitted by implantable pressure sensor 12. For example, external programmer 16 or implantable stimulator 14 may adjust stimulation parameters, such as amplitude, pulse width, and pulse rate, based on pressure information received from implantable sensor 12. In this manner, implantable stimulator 14 adjusts stimulation to either increase or reduce urinary sphincter contractility based on the actual pressure level exerted by urinary sphincter 22 on flexible tube 28 or urethra 20 on flexible tube 29. Pressure sensor 12 may transmit pressure information periodically, e.g., every few seconds, minutes or hours. In some embodiments, pressure sensor 12 may transmit pressure information when there is an abrupt change in sphincter or urethra pressure, e.g., a pressure change that exceeds a predetermined rate threshold. In addition to parameter adjustments, or alternatively, adjustment may involve on and off cycling of the stimulation in response to pressure levels indicative of a particular bladder fill stage. For example, stimulation may be turned off until the pressure level exceeds a threshold indicative of a particular fill stage of the bladder, at which time stimulation is turned on. Then, stimulation parameters may be further adjusted as the sensed pressure level changes.

External programmer 16 may be a small, battery-powered, portable device that accompanies the patient 18 throughout a daily routine. Programmer 16 may have a simple user interface, such as a button or keypad, and a display or lights. Patient 18 may initiate a voiding event, i.e., a voluntary voiding of bladder 24, via the user interface. In some embodiments, the length of time for a voiding event may be determined by pressing and holding down a button for the duration of a voiding event, pressing a button a first time to initiate voiding and a second time when voiding is complete, or by a predetermined length of time permitted by programmer 16 or implantable stimulator 14. In each case, programmer 16 causes implantable stimulator 14 to temporarily terminate stimulation so that voluntary voiding is possible.

In some embodiments, stimulator 14 may immediately resume stimulation upon completion of a voiding event, and thereafter adjust stimulation parameters based on pressure information generated by implantable sensor 12. Alternatively, stimulator 14 may terminate stimulation upon initiation of a voiding event, and recommence stimulation only after implantable pressure sensor 12 measures a decrease of pressure on flexible tube 29 in urethra 20 that corresponds to cessation or urine flow and a generally empty state of bladder 24. As a further alternative, following completion of the voiding event, stimulator 14 may wait to recommence stimulation until pressure sensor 12 detects generation of an inadequate pressure level by urinary sphincter 22, which could result in involuntary leakage. In this case, stimulator 14 recommences stimulation to enhance urinary sphincter pressure.

Implantable stimulator 14 may be constructed with a biocompatible housing, such as titanium or stainless steel, or a polymeric material such as silicone or polyurethane, and surgically implanted at a site in patient 18 near the pelvis. The implantation site may be a subcutaneous location in the side of the lower abdomen or the side of the lower back. One or more electrical stimulation leads 15 are connected to implantable stimulator 14 and surgically or percutaneously tunneled to place one or more electrodes carried by a distal end of the lead at a desired nerve site, such as a sacral nerve site within the sacrum.

In the example of FIGS. 1 and 2, sensor housing 26 of implantable pressure sensor 12 is attached to the inner wall 27 of bladder 24 near bladder neck 23. However, the attachment site for sensor housing 26 could be anywhere with access to urinary sphincter 22. With relatively long flexible tubes 28 and 29, for example, sensor housing 26 could be positioned at a greater distance from bladder neck 23. Also, in some embodiments, sensor housing 26 could be attached within urethra 20, e.g., downstream from urinary sphincter 22, although attachment of the sensor housing within bladder 24 may be desirable to avoid obstruction of the urethra. As a further alternative, as discussed above, sensor housing 26 may reside outside of bladder 24, in which case tubes 28, 29 extend through a wall of the bladder.

Figure 3:
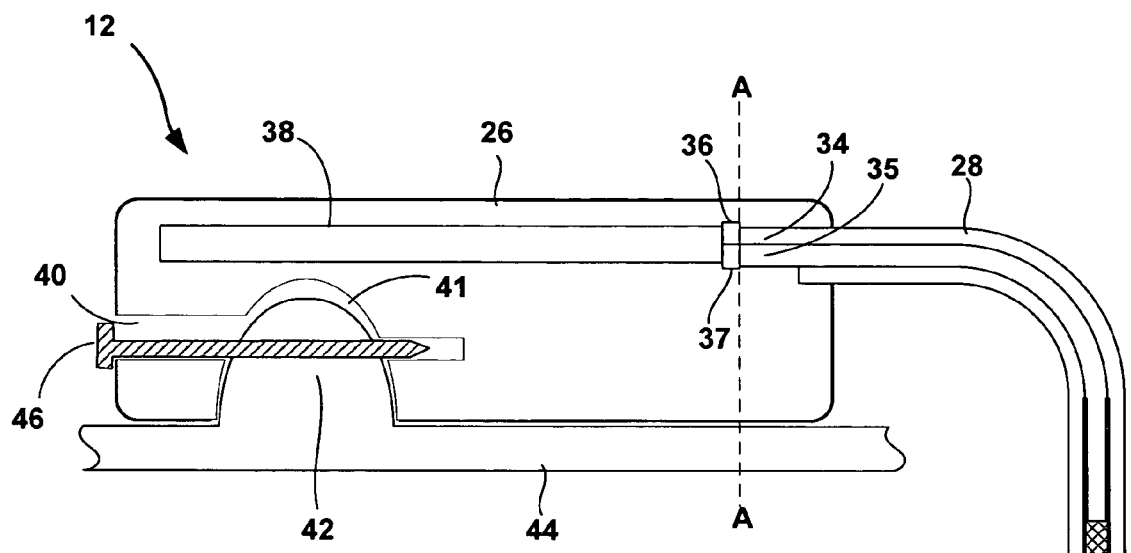
FIG. 3 is an enlarged, cross-sectional side view of the implantable pressure sensor of FIGS. 1 and 2.

FIG. 3 is an enlarged, cross-sectional side view of the implantable pressure sensor 12 of FIGS. 1 and 2. As shown in FIG. 3, sensor housing 26 receives an open end 34 of flexible tube 28 and an open end 35 of flexible tube 29. A sensing element 36 is mounted within sensor housing 26 at open end 34 to sense the pressure level of fluid tube 28, whereas a sensing element 37 is mounted within sensor housing 26 at open end 35 to sense the pressure level of fluid tube 29. Sensing elements 36 and 37 may be coupled to a circuit board 38 within sensor housing 26. In the example of FIG. 3, a substantial portion of outer tube 28 is closed off at open end 34, so that sensing element 36 communicates with the interior of the outer tube via only a small opening. This arrangement facilitates mounting of sensing elements 36 and 37 in side-by-side relationship.

Figure 4:
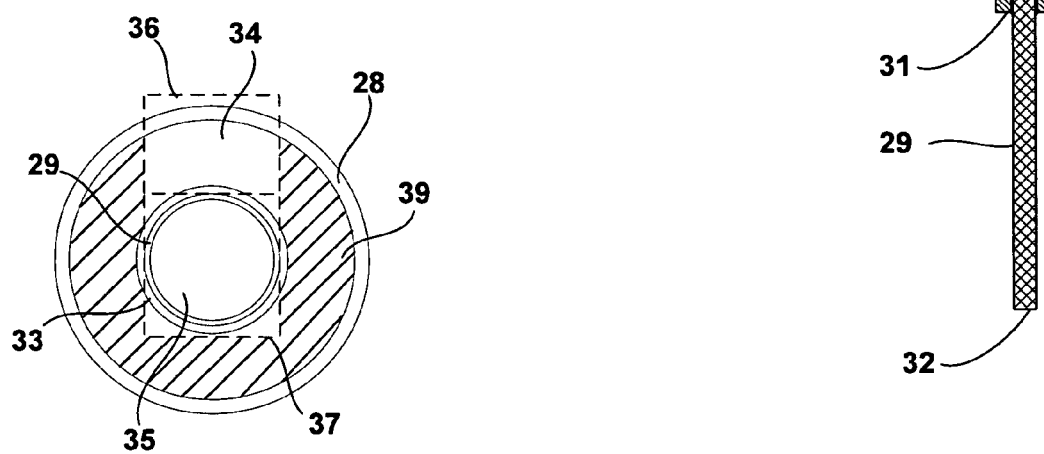
FIG. 4 is a cross-sectional end view of the flexible tubes of the implantable pressure sensor shown in FIG. 3, taken along line A-A of FIG. 3

FIG. 4 is a cross-sectional end view of tubes 28, 29, taken along line A-A, illustrating the closing of a substantial portion of outer tube 28 and the alignment of sensing elements 36, 37 with open portions of the tubes 28, 29. As shown in FIG. 4, an extensive portion of tube 28 is closed off, as indicated by cross-hatched region 39, so that only open end 34 is in fluid communication with sensing element 36. In other embodiments, sensing elements 36, 37 could be concentrically arranged such that sensing element 37 communicates with the open end 35 of inner tube 29, and sensing element 36 has an annular shape that communicates with an annular open end of outer tube 28. As also shown in FIG. 4, a substantially rigid interface tube 33 separates outer tube 28 and inner tube 29 so that pressure exerted against the outer tube by urinary sphincter 22 does not significantly affect the pressure within the inner tube. In this manner, pressure can be independently measured for urinary sphincter 22 and within urethra 20 by tubes 28 and 29, respectively. In some embodiments, flexible tubes 28, 29 may be coated to avoid calcification.

In this exemplary embodiment, flexible tubes 28 and 29 are filled with respective fluids. Upon exertion of force on flexible tube 28 by urinary sphincter 22, the resulting increase in fluid pressure is transduced by sensing element 36. Similarly, sensing element 37 transduces fluid pressure changes within flexible tube 29 in response to exertion of force within urethra 20. Inward deformation of flexible tube 28 causes an elevation in the internal pressure of the tube. Flexible tube 29 operates in a similar manner. Sensing element 36 senses the elevation in pressure at open end 34 of flexible tube 28, and generates a pressure signal that represents the pressure level. Although end 34 is referred to as "open," it is sealed by sensing element 36. Consequently, deformation of flexible tube 28 causes a change in the tube volume, and hence pressure changes in the fluid 30 within the tube.

Similar changes occur when pressure is exerted on flexible tube 29, which sensing element 37 measures. Flexible tube 29 resides inside tube 28 and is longer and of smaller diameter than flexible tube 28. Note that the interface between flexible tubes 28 and 29 may be more rigid than the tubes. Rigid tube 33 is incorporated to provide circumferential stiffness to the outside of tube 29 to allow sphincter 22 to exert force on flexible tube 28 without affecting the pressure within tube 29. Rigid tube 33 may be made of any number of materials including a more dense polyurethane or light metal alloy, and preferably a material that provides substantial circumferential stiffness over flexible tubes 28 and 29 while still enabling axial bending.

Flexible tubes 28 and 29 may be formed from a variety of flexible materials, including polyurethane or silicone. The flexibility of tubes 28 and 29 permits them to conform to contours within bladder neck 23, and deform in response to pressure exerted by urethra 20 and urinary sphincter 22 at bladder neck 23. In particular, urinary sphincter 22 exerts pressure inward against the outer wall of urethra 20. In turn, the inner wall of urethra 20 exerts pressure inward against the outer walls of flexible tubes 28 and 29, causing the walls of the tubes to deform and compress inward.

Sensing elements 36 or 37 may include a strain gauge sensor, e.g., formed by thin film deposition on a flexible membrane. The strain gauge sensor transduces pressure changes into electrical signals for processing and analysis within pressure sensor 12. Circuit board 38 may include processing electronics to process signals generated by sensing element 34, and generate pressure information based on the signals monitoring the pressure level of each tube. In addition, circuit board 38 may include telemetry circuitry for wireless telemetry with stimulator 14, external programmer 16, or both.

Sensing elements 36 and 37, in some embodiments, may be constructed as a membrane that carries a resistive strain gauge or piezoelectric element selected to be effective as a pressure transducer. Upon deformation of the membrane, in response to pressure levels within their respective tubes, the sensing element produces an electrical signal. When sphincter 22 closes, the flexible tube deforms and the pressure inside the tube increases. The higher pressure forces the membrane within the sensing element to deform, thus producing an electrical signal change and enabling implanted pressure sensor 12 to measure sphincter closing pressure.

The fluid 30 contained within each tube may be a liquid or gas, or a combination of liquid and gas. For example, flexible tubes 28 and 29 could be filled with saline, distilled water, oxygen, air or any other biocompatible fluid. Preferably, the fluid 30 within the tubes is generally non-compressible. Fluid 30 tends to exhibit an elevation in pressure as the walls of tubes 28 and 29 are deformed during constriction of urinary sphincter 22 or urethra 20. Conversely, fluid 30 exhibits a reduction in pressure as urinary sphincter 22 and urethra 20 relaxes. In each case, the pressure level is transduced by a sensing element 36, 37 for each respective tube 28, 29.

In some embodiments, the flexible tubes 28 and 29 may contain fluid as described previously while arranged in a different conformation. Another configuration of tubes 28 and 29 may include two separate tubes adjacent to one another instead of residing within one another. The tubes may also be constructed of a non-circular cross-section. Some cross-sectional shapes may include polygons or perhaps two hemispherical tubes to create one circular cross-section when placed next to each other inside of the patient. However, a circular cross-section may be desirable to promote effective sealing of urinary sphincter 22 against the outer surface of the tube or tubes.

Flexible tubes 28 and 29 may be provided with different dimensions selected for patients having different anatomical dimensions. In particular, implantable pressure sensor 12 may be constructed with flexible tubes 28 and 29 having different lengths of diameters. Different tube lengths may be necessary given the distance between the attachment site of sensor housing 26 and urinary sphincter 22, either to ensure that the tubes reach the sphincter and urethra or do not extend too far down urethra 20. Multiple diameters may also be necessary to allow a dysfunctional sphincter 22 to close completely or to allow tubes 28 and 29 to be placed into a narrow urethra 20. The dimensions may be fixed for a given pressure sensor 12, as a complete assembly. Alternatively, tubes of different sizes may be attached to a pressure sensor housing 26 by a physician prior to implantation.

In general, for male patients, flexible tubes 28, 29 may each have a length of less than approximately 9 cm and more preferably less than approximately 7 cm. For female patients, flexible tubes 28, 29 may each have a length of less than approximately 7 cm and more preferably less than approximately 5 cm. In some embodiments, flexible tubes 28, 29 may each have a length of approximately 0.5 cm to 3 cm. In each case, flexible tube 29 may be somewhat longer than tube 28, e.g., by approximately 1 to 3 cm. The lengths of tubes 28, 29 may vary according to the anatomy of the patient, and may vary between male, female and pediatric patients. In addition, tube 28 may have an outer diameter in a range of approximately 1 to 3 mm, whereas tube 29 may have an outer diameter in a range of approximately 0.5 to 2 mm. The walls of tubes 28, 29 may be relatively thin to ensure sufficient deformation and conformability, yet thick enough to ensure structural integrity. As an example, the thickness of the walls of tubes 28, 29 may be in a range of approximately 0.1 mm to 0.3 mm.

Sensor housing 26 may be made from a biocompatible material such as titanium, stainless steel, or nitinol, or a polymeric material such as silicone or polyurethane. Another material for fabrication of sensor housing 26 is a two-part epoxy. An example of a suitable epoxy is a two-part medical implant epoxy manufactured by Epoxy Technology, Inc., mixed in a ratio of 10 grams of resin to one gram of activator. In general, sensor housing 26 contains no external openings, with the exception of the opening to receive flexible tubes 28 and 29, thereby protecting sensing element 36, sensing element 37 and circuit board 38 from the environment within bladder 24. The proximal, open end 34, 35 of each respective flexible tube 28, 29 resides within sensor housing 26 while the distal, closed ends reside outside of the sensor housing. The opening in sensor housing 26 that receives open end 34 and 35 of flexible tubes 28 and 29, respectively, may be sealed to prevent exposure of interior components.

Attaching implantable pressure sensor 12 to the mucosal lining of bladder 24 may be accomplished in a variety of ways, but preferably is completed in a manner that will not excessively injure bladder 24. Preferably, attachment should cause limited inflammation no adverse physiological modification, such as tissue infection or a loss in structural integrity of bladder 24. However, it is desirable that implantable pressure sensor 12 also be attached securely to the attachment site in order to provide an extended period of measurement without prematurely loosening or detaching from the intended location.

As an example, with further reference to FIG. 3, sensor housing 26 may contain a vacuum cavity 41 that permits a vacuum to be drawn by a vacuum channel 40. The vacuum is created by a deployment device having a vacuum line in communication with vacuum channel 40. The vacuum draws a portion 42 of the mucosal lining 44 of bladder 24 into vacuum cavity 41. Once the portion 42 of mucosal lining 44 is captured within vacuum cavity 41, a fastening pin 46 is driven into the captured tissue to attach sensor housing 26 within bladder 24. Fastening pin 46 may be made from, for example, stainless steel, titanium, nitinol, or a high density polymer. The shaft of pin 46 may be smooth or rough, and the tip may be a sharp point to allow for easy penetration into tissue. Fastening pin 46 may be driven into housing 26 and the portion 42 of mucosal lining 44 under pressure, or upon actuation by a push rod, administered by a deployment device.

In some embodiments, fastening pin 46 may be manufactured from a degradable material that the breaks down over time, e.g. in the presence of urine, to release implantable pressure sensor 12 within a desired time period after attachment. In still another embodiment, implantable pressure sensor 12 may be attached without the use of a penetrating rod but with a spring-loaded clip to pinch trapped mucosal lining 44 within cavity 41. A variety of other attachment mechanisms, such as pins, clips, barbs, sutures, helical screws, surgical adhesives, and the like may be used to attach sensor housing 26 to mucosal lining 44 of bladder 24.

Figure 5:
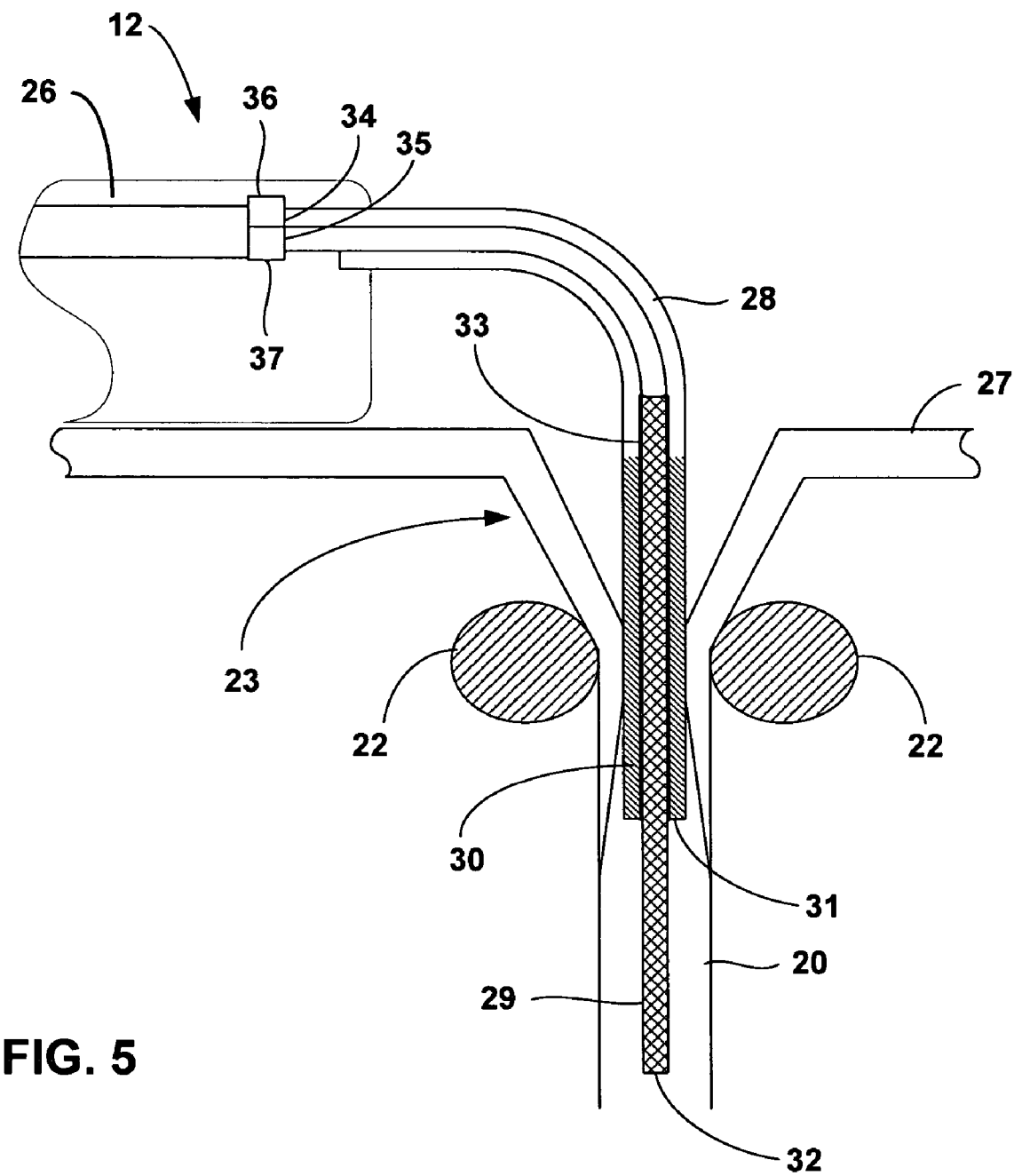
FIG. 5 is a schematic diagram illustrating placement of an implantable pressure sensor with two flexible tubes extending through the internal urinary sphincter and into the urethra of a patient.

FIG. 5 is a schematic diagram illustrating placement of an implantable pressure sensor 12 with two flexible tubes 28 and 29 extending through the urinary sphincter 22 of a patient 18. In the example of FIG. 5, flexible tubes 28 and 29 leave bladder 24 through bladder neck 23 and pass through internal urinary sphincter 22 and into urethra 20. In general, sphincter 22 is an annulus shaped muscle that surrounds the portion of urethra 20 below bladder neck 23 and constricts to make the urethral walls meet and thereby close urethra 20 to prevent involuntary urine leakage from bladder 24. Upon constriction of sphincter 22, the walls of urethra 20 close onto flexible tube 28 to increase the internal pressure of the tube, which provides a measurement of the closing pressure of sphincter 22. Flexible tube 29 provides a measurement of the pressure of urethra 20, which may fluctuate as a function of the pressure of urine flowing within the urethra. Because the tubes have a circular cross-section and a small diameter, the closed sphincter 22 is able to substantially seal urethra 20 around outer, flexible tube 28.

When sphincter 22 is relaxed, implantable pressure sensor 12 may be used to measure the pressure of fluid in urethra 20 via inner, flexible tube 29. The open sphincter 22 allows urine to be passed out of the urethra and patient 18. Flexible tube 29 is under the same pressure as the urethra and can allow implantable pressure sensor 12 to measure this urethral pressure. This feature may allow monitoring of urinary dysfunctions due to pressure during voiding events and may also be used by implantable stimulator 14 to detect the end of a voiding event by measuring decrease of urethral pressure as an indication of reduced urine flow, and hence completion of bladder emptying.

As shown in FIG. 5, the placement of tubes 28 and 29 does not significantly interfere with normal bladder function. When urinary sphincter 22 relaxes, bladder function is generally unimpaired and fluid flow to urethra 20 can occur normally, as tubes 28, 29 allow enough room for urine to pass and exit bladder 24 via urethra 20. Due to varying sizes and shapes of patient anatomy, tubes 28, 29 may be manufactured in a variety of lengths and diameters. In particular, female, male, and pediatric patients may present a range of anatomical differences that require different lengths and diameters for tubes 28, 29.

Figure 6:
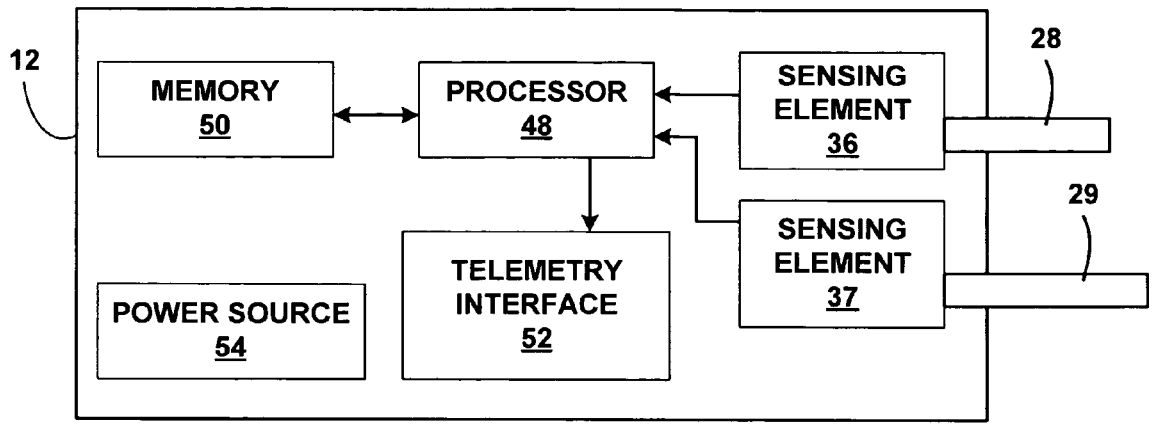
FIG. 6 is functional block diagram illustrating various components of an exemplary implantable pressure sensor.

FIG. 6 is functional block diagram illustrating various components of an exemplary implantable pressure sensor 12. In the example of FIG. 6, implantable pressure sensor 12 includes a sensing elements 36 and 37, processor 48, memory 50, telemetry interface 52, and power source 54. Sensors 36 and 37 transform mechanical deformation from tubes 28 and 29, respectively, into electrical signals representative of closing pressure of urinary sphincter 22 and fluid pressure within urethra 20. The electrical signals may be amplified, filtered, and otherwise processed as appropriate by electronics within sensor 12. In some embodiments, the signals may be converted to digital values and processed by processor 48 before being stored in memory 50 or sent to implantable stimulator 14 or external programmer 16 as pressure information via telemetry interface 52.

Memory 50 stores instructions for execution by processor 48 and pressure information generated by sensing elements 36 and 37. Pressure information may then be sent to implantable stimulator 14 or external programmer 16 for long-term storage and retrieval by a user. Memory 50 may include either a single memory or separate memories for storing instructions and pressure information. In addition, processor 48 and memory 50 may implement loop recorder functionality in which processor 48 overwrites the oldest contents within the memory 50 with new data as storage limits are met.

Processor 48 controls telemetry interface 52 to send pressure information to implantable stimulator 14 or programmer 16 on a continuous basis, at periodic intervals, or upon request from the implantable stimulator or programmer. Wireless telemetry may be accomplished by radio frequency (RF) communication or proximal inductive interaction of pressure sensor 12 with programmer 16.

Power source 54 delivers operating power to the components of implantable pressure sensor 12. Power source 54 may include a battery and a power generation circuit to produce the operating power. In some embodiments, the battery may be rechargeable to allow extended operation Recharging may be accomplished through proximal inductive interaction between an external charger and an inductive charging coil within sensor 12. In some embodiments, power requirements may be small enough to allow sensor 12 to utilize patient motion and implement a kinetic energy-scavenging device to trickle charge a rechargeable battery. In other embodiments, traditional batteries may be used for a limited period of time. As a further alternative, an external inductive power supply may transcutaneously power sensor 12 whenever pressure measurements are needed or desired.

Figure 7:
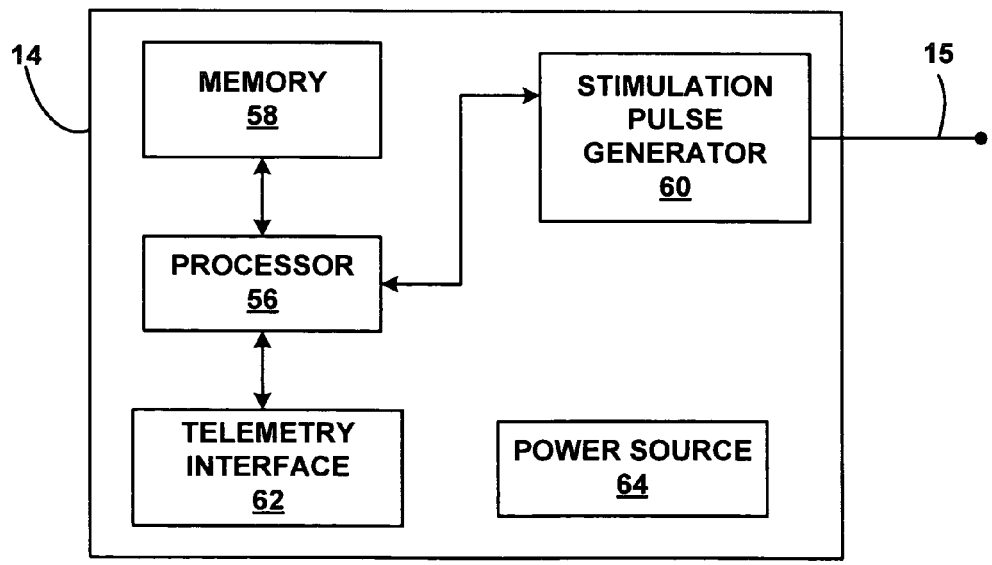
FIG. 7 is a functional block diagram illustrating various components of an implantable stimulator.

FIG. 7 is a functional block diagram illustrating various components of an implantable stimulator 14. In the example of FIG. 7, stimulator 14 includes a processor 56, memory 58, stimulation pulse generator 60, telemetry interface 62, and power source 64. Memory 58 stores instructions for execution by processor 56, stimulation therapy data, and pressure information received from pressure sensor 12 via telemetry interface. Pressure information is received from pressure sensor 12 and may be recorded for long-term storage and retrieval by a user, or adjustment of stimulation parameters, such as amplitude, pulse width or pulse rate. Memory 58 may include separate memories for storing instructions, stimulation parameter sets, and pressure information.

Processor 56 controls stimulation pulse generator 60 to deliver electrical stimulation therapy and telemetry interface 62 to exchange information with sensor 12 and programmer 16. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

Based on pressure information received from sensor 12, processor 56 interprets the information and determines whether any therapy parameter adjustments should be made. For example, processor 56 may compare the pressure level to one or more thresholds, and then take action to adjust stimulation parameters based on the pressure level. Information may be received from sensor 12 on a continuous basis, at periodic intervals, or upon request from stimulator 14 or external programmer 16. Alternatively, or additionally, pressure sensor 12 may transmit pressure information when there is an abrupt change in the pressure level, e.g., at the onset of involuntary leakage.

Processor 56 modifies parameter values stored in memory 58 in response to pressure information from sensor 12, either independently or in response to programming changes from external programmer 16. Stimulation pulse generator 60 provides electrical stimulation according to the stored parameter values via a lead 15 implanted proximate to a nerve, such as a sacral nerve. Processor 56 determines any parameter adjustments based on the pressure information obtained form sensor 12, and loads the adjustments into memory 58 for use in delivery of stimulation.

As an example, if the pressure information indicates an inadequate sphincter closing pressure, processor 56 may increase the amplitude, pulse width or pulse rate of the electrical stimulation applied by stimulation pulse generator 60 to increase stimulation intensity, and thereby increase sphincter closing pressure. If sphincter closing pressure is adequate, processor 56 may implement a cycle of downward adjustments in stimulation intensity until sphincter closing pressure becomes inadequate, and then incrementally increase the stimulation upward until closing pressure is again adequate. In this way, processor 56 converges toward an optimum level of stimulation. Adjustment may be made by adjusting the parameters, or switching to a different set of parameters. Although processor 56 is described in this example as adjusting stimulation parameters, it is noted that the adjustments may be generated by external programmer 16.

The adequacy of closing pressure is determined by reference to the pressure information obtained from sensor 12. Sphincter pressure may change due to a variety of factors, such as an activity type, activity level or posture of the patient 18. Hence, for a given set of stimulation parameters, the efficacy of stimulation may vary in terms of sphincter pressure, due to changes in the physiological condition of the patient. For this reason, the continuous or periodic availability of pressure information from implantable sensor 12 is highly desirable.

With this pressure information, stimulator 14 is able to respond to changes in sphincter pressure with dynamic adjustments in the stimulation parameters delivered to the patient 18. In particular, processor 56 is able to adjustment parameters in order to cause constriction of sphincter 22 and thereby avoid involuntary leakage. In some cases, the adjustment may be nearly instantaneous, yet prevent leakage. As an example, if patient 18 laughs, coughs, or bends over, the resulting force on bladder 24 could overcome the closing pressure of urinary sphincter 22. If pressure sensor 12 indicates an abrupt change in sphincter pressure, however, stimulator 14 can quickly respond by more vigorously stimulating the sacral nerves to increase sphincter closing pressure.

In general, if sphincter 22 is not constricting enough to effectively close urethra 20, processor 56 may dynamically increase the level of therapy to be delivered. Conversely, if sphincter 22 is consistently achieving effective constriction, processor 56 may incrementally reduce stimulation, e.g., to conserve power resources.

As in the case of sensor 12, wireless telemetry in stimulator 14 may be accomplished by radio frequency (RF) communication or proximal inductive interaction of pressure stimulator 14 with implantable pressure sensor 12 or external programmer 16. Accordingly, telemetry interface 62 may be similar to telemetry interface 52. Also, power source 64 of stimulator 14 may be constructed somewhat similarly to power source 54. For example, power source 64 may be a rechargeable or non-rechargeable battery, or alternatively take the form of a transcutaneous inductive power interface.

Figure 8:
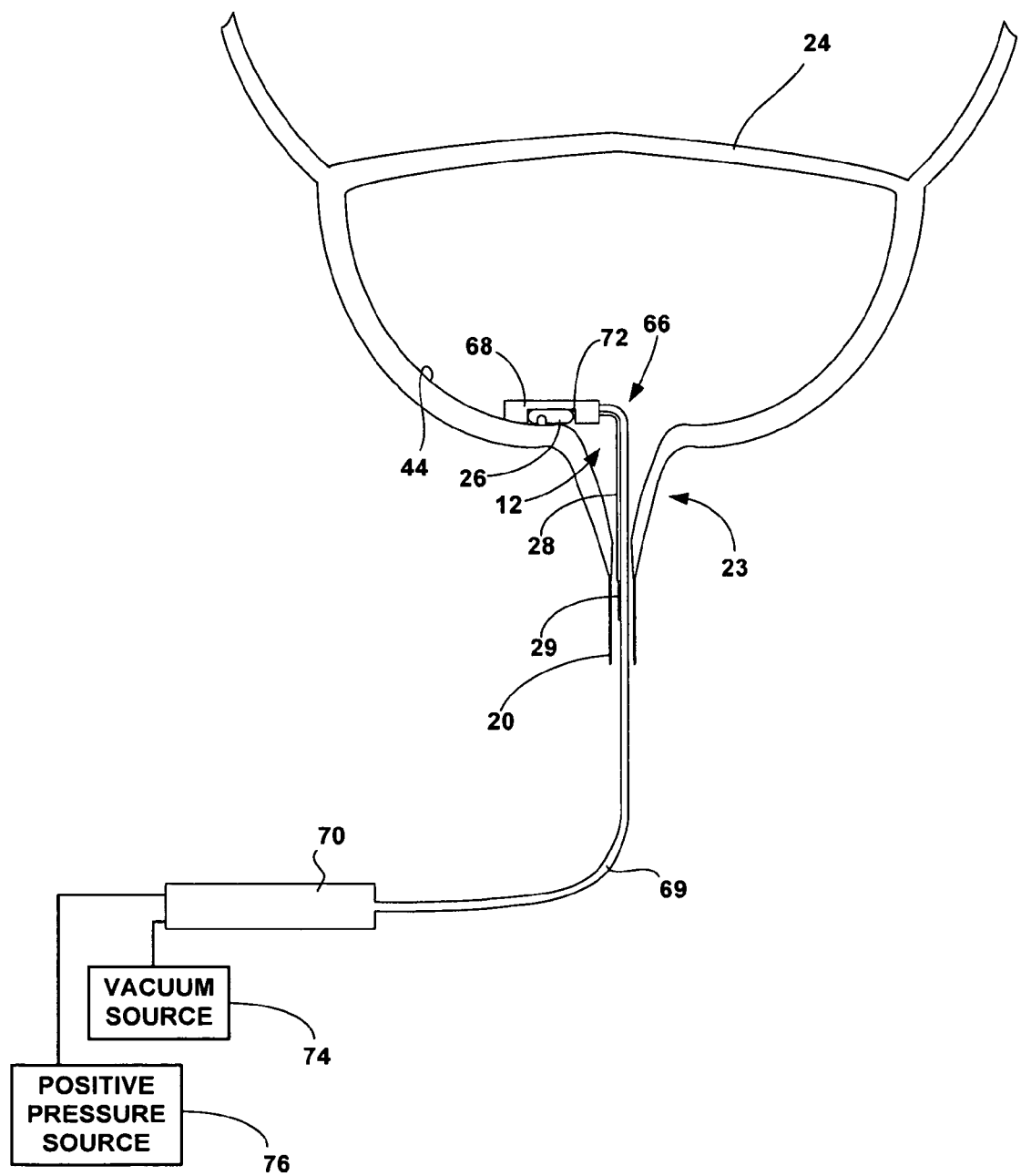
FIG. 8 is a schematic diagram illustrating cystoscopic deployment of an implantable pressure sensor via the urethra.

FIG. 8 is a schematic diagram illustrating cystoscopic deployment of an implantable pressure sensor 12 via the urethra 20 using a deployment device 66. Pressure sensor 12 may be surgically implanted. However, cystoscopic implantation via urethra is generally more desirable in terms of patient trauma, recovery time, and infection risk. In the example of FIG. 8 deployment device 66 includes a distal head 68, a delivery sheath 69 and a control handle 70. Deployment device 66 may be manufactured from disposable materials for single use applications or more durable materials for multiple applications capable of withstanding sterilization between patients.

As shown in FIG. 8, distal head 68 includes a cavity 72 that retains sensor housing 26 of implantable pressure sensor 12 for delivery to a desired attachment site within bladder 24. Sensor housing 26 may be held within cavity 72 by a friction fit, vacuum pressure, or a mechanical attachment. In each case, once distal head 68 reaches the attachment site, sensor housing 26 may be detached. Sheath 69 is attached to distal head 68 and is steerable to navigate urethra 20 and guide the distal head into position. In some embodiments, sheath 69 and distal head 68 may include cystoscopic viewing components to permit visualization of the attachment site. In other cases, external visualization techniques such as ultrasound may be used. Sheath 68 may include one or more steering mechanisms, such as wires, shape memory components, or the like, to permit the distal region adjacent distal head 68 to turn abruptly for access to the mucosal lining of bladder 24.

A control handle 70 is attached to sheath 69 to aid the physician in manually maneuvering deployment device 66 throughout urethra 20 and bladder 24. Control handle 70 may have a one or more controls that enable the physician to contort sheath 69 and allow for deployment device 66 to attach pressure sensor housing 26 to the mucosal lining of bladder 24 and then release the sensor housing to complete implantation. A vacuum source 74 supplies negative pressure to a vacuum line within sheath 69 to draw tissue into the vacuum cavity defined by sensor housing 66. A positive pressure source 76 supplies positive pressure to a drive a fastening pin into the tissue captured in the vacuum cavity.

Deployment device 66 enters patient urethra 20 to deliver pressure sensor 12 and implant it within bladder 24. First, the physician must guide distal head 68 through the opening of urethra 20 in patient 18. Second, distal head 68 continues to glide up urethra 20 and past the relaxed internal sphincter 22. Distal head 68 is then pushed through bladder neck 23 and into bladder 24, for access to an appropriate site to attach pressure sensor 12. Using actuators built into control handle 70, sheath 69 is bent to angle distal head 68 into position. Again, sheath 69 may be steered using control wires, shape memory alloys or the like.

As pressure sensor 12 is guided into place against the mucosal wall 44 of bladder 24, a physician actuates control handle 70 to attach sensor 12 to mucosal wall 44 and then release the attached sensor. Upon attachment, pressure sensor 12 is implanted within bladder 24 of patient 18 and deployment device 66 is free to exit the bladder. Exemplary methods for attachment and release of sensor 12, including the use of both vacuum pressure and positive pressure, will be described in greater detail below. Although FIG. 8 depicts cystoscopic deployment of pressure sensor 12, surgical or laparoscopic implantation techniques alternatively may be used. Also, in some embodiments, sensor housing 26 may be implanted outside of bladder 24.

Figure 9:
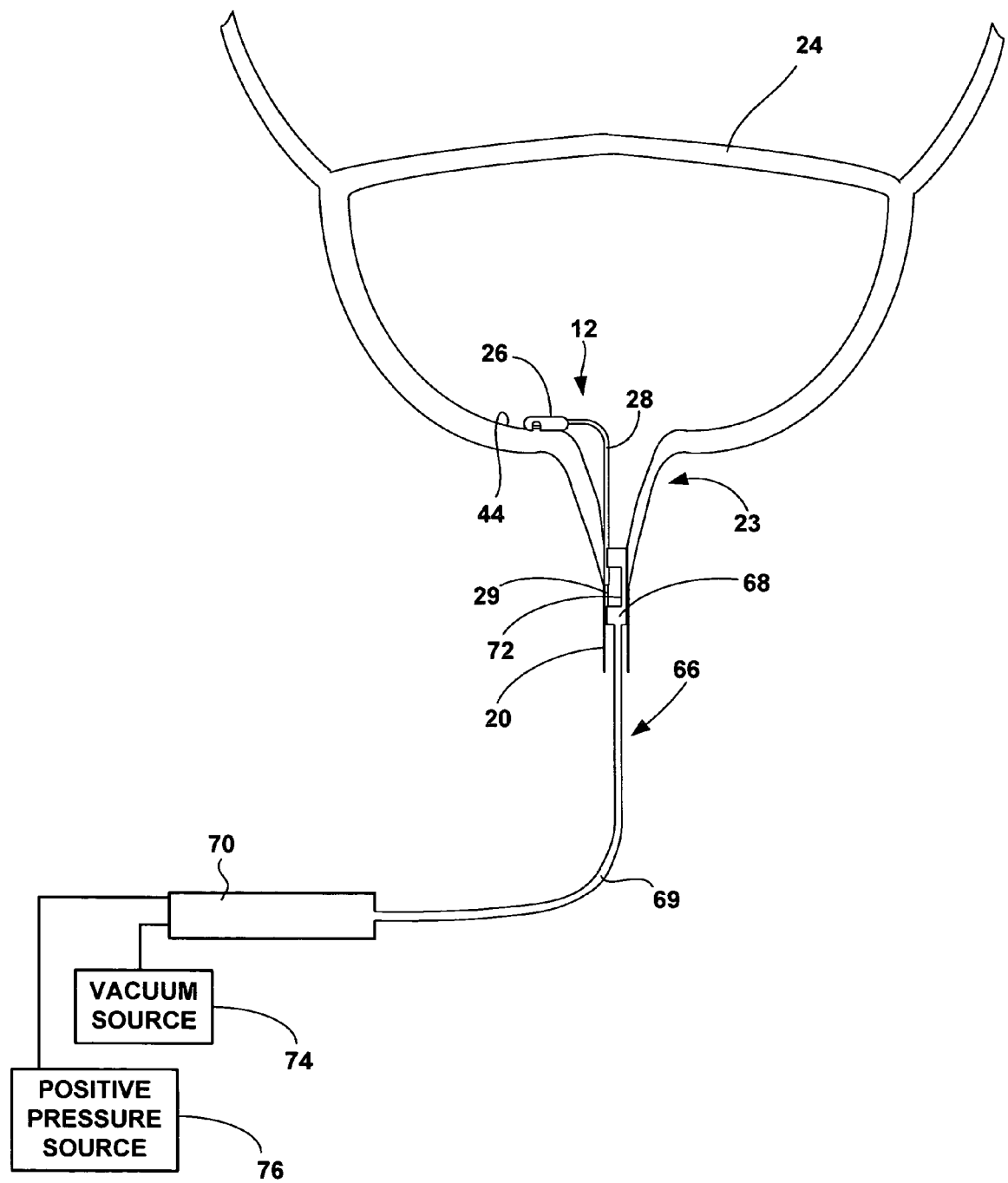
FIG. 9 is a schematic diagram illustrating retraction of a deployment device upon fixation of a pressure sensor within a patient's urinary tract.

FIG. 9 is a schematic diagram illustrating retraction of deployment device 66 upon fixation of pressure sensor 12 within the urinary tract of patient 18. Once the sensor 12 is released, flexible tubes 28 and 29 remain attached to sensor housing 26. During removal of deployment device 66, tubes 28 and 29 maintain their position within bladder neck 23 adjacent sphincter 22. As deployment device 66 is removed, both tubes pass through a guide channel formed in the deployment device. The guide channel ensures that flexible tubes 28 and 29 remain pinned between distal head 68 and the wall of bladder 24.

As distal head 68 slides through sphincter 22 and urethra 20, flexible tubes 28 and 29 release from deployment device 66 and are left in place within the urethra in the region proximate urinary sphincter 22. Deployment device 66 may then be completely withdrawn past the external urinary sphincter and out of the remainder of urethra 20. In the example of FIG. 9, both flexible tubes 28 and 29 are suspended by device housing 26, which is attached to mucosal wall 44, and is held in place by pressure exerted against the urethral wall by urinary sphincter 22. In other embodiments, tubes 28 and 29 may be kept in place using other techniques such as actively attaching the tubes to the side of urethra 20, e.g., with sutures or other anchor mechanisms.

In a preferred embodiment, sheath 69 and distal head 68 may be disposable. Disposable devices that come into contact with tissues and fluids within the patient greatly decrease the possibility of infection in implantable devices. Control handle 70 does not come into contact with body fluids of patient 18 and may be used for multiple patients. In another embodiment, the entire deployment device 66 may be manufactured out of robust materials intended for multiple uses. The device would then need to be sterilizable between uses. In still a further embodiment, the features of distal head 68 may be incorporated into pressure sensor 12. In this configuration, pressure sensor 12 may be larger in size but would include the necessary elements for attachment within the device. After attachment, the entire sensor 12 would detach from sheath 69, making removal of deployment device 66 easier on patient 18.

After the useful life of implantable pressure sensor 12 is complete or it is no longer needed within patient 18, it can be removed from patient 18 in some manner. As an example, deployment device 66 may be reinserted into patient 18, navigated into bladder 24, and reattached to pressure sensor 12. Deployment device 66 may then be withdrawn from the bladder 24 and urethra 20, explanting sensor 12, including housing 26 and flexible tubes 28 and 29, from patient 18. In another embodiment, as mentioned with respect to FIG. 3, the attachment method of pressure sensor 12 to bladder 24 may involve degradable materials, such as a biodegradable fixation pin. After a certain period of time exposed to urine in the bladder 24, the fixation material may structurally degrade and allow pressure sensor 12 to be released from the mucosal wall 44 of bladder 24. In some embodiments, sensor 12 may be sized sufficiently small to follow urine out of the bladder, urethra, and body during a voiding event. In other embodiments, sensor housing 26 or either of tubes 28, 29 may carry a suture-like loop that can be hooked by a catheter with a hooking element to withdraw the entire assembly from patient 18 via urethra 20. In still further embodiments, such a loop may be long enough to extend out of the urethra, so that the loop can be grabbed with an external device or the human hand to pull the sensor 12 out of the patient.

Figure 10:
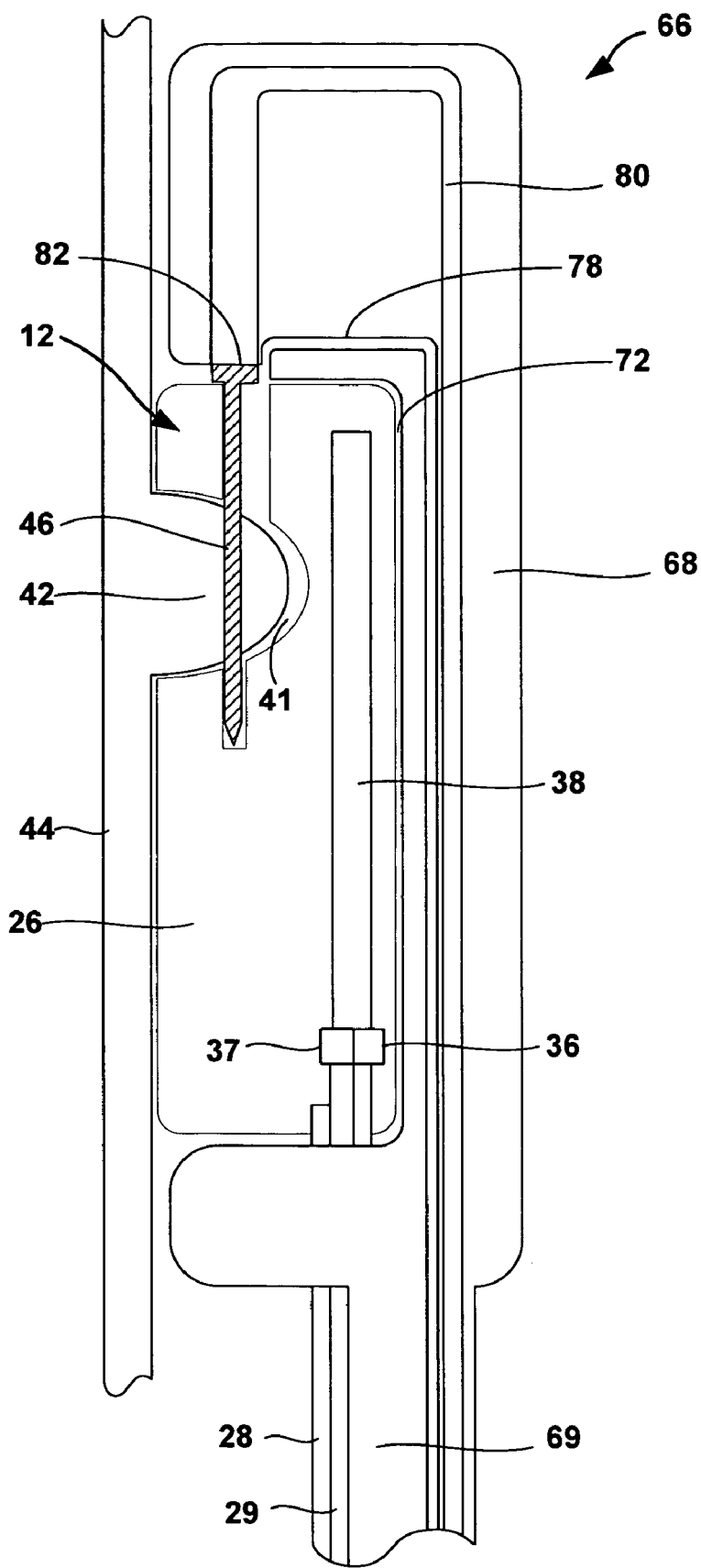
FIG. 10 is a cross-sectional side view of a deployment device during deployment and fixation of a pressure sensor.

FIG. 10 is a cross-sectional side view of distal head 68 of deployment device 66 during deployment and fixation of pressure sensor 12. In the example of FIG. 10, distal head 68 includes a vacuum line 78 and a positive pressure line 80. Vacuum line 78 is coupled to vacuum source 74 via a tube or lumen extending along the length of sheath 69. Similarly, positive pressure line 80 is coupled to positive pressure source 76 via a tube or lumen extending along the length of sheath 69. Vacuum line 78 is in fluid communication with vacuum cavity 41, and permits the physician to draw a vacuum and thereby capture a portion 42 of mucosal lining 44 within the vacuum cavity. Although vacuum line 78 is shown as being coupled laterally to vacuum cavity 41, the vacuum line could access the vacuum cavity from another direction, such as the top of the vacuum cavity. Positive pressure line 80 permits the physician to apply a pulse of high pressure fluid, such as a liquid or a gas, to drive fixation pin 46 into sensor housing 26 and through the portion 42 of mucosal lining 44. Pin 46 thereby fixes sensor housing 26 to mucosal lining 44. In some embodiments, a membrane mounted over an opening of positive pressure line 80 may be punctured by pin 46.

Flexible tubes 28 and 29 reside within a channel (not shown in FIG. 10) of sheath 69 prior to detachment or sensor 12 from distal head 68. Once fixation pin 46 attaches sensor 12 to bladder 24, vacuum line 78 is no longer needed. However, in some embodiments, vacuum line 78 may be used to detach pressure sensor 12 from distal head 68 of deployment device 66. By terminating vacuum pressure, or briefly applying positive pressure through vacuum line 78, for example, head 68 may separate from sensor 12 due to the force of the air pressure. In this manner, vacuum line 78 may aid in detachment of sensor 12 prior to withdrawal of deployment device 66.

As described previously in FIG. 3, fixation pin 46 punctures mucosal lining 44 for fixation of sensor 12. While the force of this fixation may vary with patient 18, deployment device 66 provides adequate force for delivery of pin 46. In an exemplary embodiment, positive pressure line 80 is completely sealed and filled with a biocompatible fluid (such as water, saline solution or air). Sealing the end of positive pressure line 80 is a head 82 on fixation pin 46. Head 82 is generally able to move within positive pressure line 80 much like a piston. Force to push fixation pin 46 through the portion 42 of mucosal lining 44 captured in vacuum cavity 41 is created by application of a pulse of increased fluid pressure within positive pressure line 80. For example, the physician may control positive pressure source 76 via control handle 70. This simple delivery method may provide high levels of force, allow multiple curves and bends in sheath 69, and enable a positive pressure line 80 of many shapes and sizes.

In an alternative embodiment, a flexible, but generally incompressible, wire may placed within positive pressure line 80 and used to force fixation pin 46 through the captured portion 42 of mucosal lining 44. This wire presents compressive force from control handle 70 directly to the head 82 of fixation nail 46. This approach may eliminate any safety risk of pressurized fluids entering patient 18 or, in some embodiments, permit retraction of pin 46 after an unsuccessful fixation attempt. The flexible wire may be attached to pin 46 and pulled back to remove the pin from capture mucosal tissue 42. The flexible wire may be sheared from fixation nail 46 for detachment purposes as distal head 68 releases sensor 12. This detachment may be facilitated by a shearing element and low shear stress of the wire.

In FIG. 10, deployment device 66 illustrates flexible tubes 28 and 29 on the same end of housing 26 as sheath 69, while the fixation structures are located in the opposite, or distal end of distal head 68. In some embodiments, it may be desirable for pressure sensor 12 to be deployed with tube 28 located at the distal end of head 68 and the fixation structures located near sheath 69. In still other embodiments, the fixation structures and both tubes may be located on the same end of pressure sensor 12.

In some embodiments, deployment device 66 may include a small endoscopic camera in the distal head 68. The camera may enable the physician to better guide deployment device 66 through urethra 20, past sphincter 22, and to a desired attachment location of bladder 24 in less time with more accuracy. Images may be displayed using video fed to a display monitor.

Figure 11:
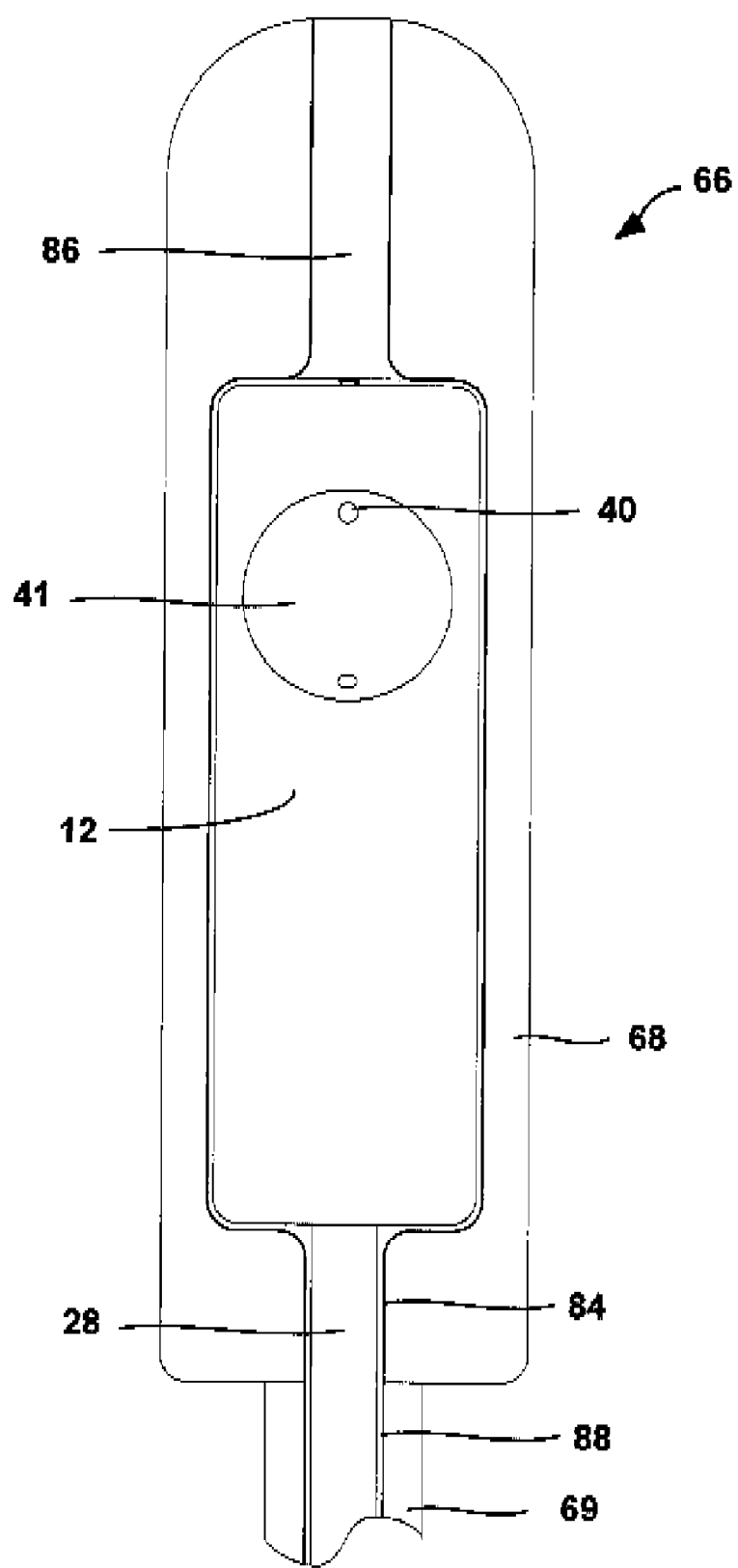
FIG. 11 is a cross-sectional bottom view of the deployment device of FIG. 10 before attachment of the pressure sensor.

FIG. 11 is a cross-sectional bottom view of the distal head 68 of deployment device 66 of FIG. 10 before attachment of pressure sensor 12. As shown in FIG. 11, distal head 68 includes proximal tube channel 84 to accommodate flexible tubes 28 and 29 during placement of sensor 12 and distal tube channel 86 to accommodate the flexible tube during retraction of deployment device 66. In addition, sheath 69 includes a sheath channel 88 to accommodate flexible tube 28. Channels 84, 86, 88 serve to retain tube 28 during delivery of sensor 12 to an attachment site.

Distal head 68 is rounded on both sides at the distal end to permit easier entry of deployment device into areas of patient 18. Head 68 may also be lubricated before delivery to facilitate ease of navigation. On the proximal end of head 68, proximal tube channel 84 runs through the head for unimpeded removal of tubes 28 and 29 during detachment of pressure sensor 12. This channel may be U-shaped, e.g. closed on 3 sides. In some embodiments, proximal tube channel 84 may be an enclosed hole in which both tubes resides and glides through upon deployment device 30 removal.

Sheath channel 88 is formed within sheath 69 to allow tube 28 to stay in place during delivery of pressure sensor 12. In this embodiment, tube 28 is only partially retained within channel 88. In some embodiments, sheath channel 88 may be deeper to allow tube 28 to lie completely within sheath 69. In other embodiments, sheath channel may be completely enclosed such that tubes 28 and 29 must glide out of the channel after attachment.

Distal channel 86 in distal end of head housing 68 is not used by either tube 28 or 29 before attachment. The purpose of this open channel is to allow tubes 28 and 29 to glide through it while head 68 is removed from bladder 24. As head 68 slides back past pressure sensor 12, tube 28 will slide through channel 86 and head housing 68 will keep tube 28 between the wall of bladder 24 and head 68 until head 68 has been removed beyond sphincter 22. Tube 29 may then be ensured correct placing within urethra 20.

Some embodiments of tubes 28 and 29 include multiple length and diameter combinations which would lead to modifications in channels 84, 86 and 88. Accordingly, the channels 86, 88 described herein may be of different diameters or lengths to properly house each tube. One embodiment may include flexible housing channels to accommodate a wide variety of tube dimensions. Further embodiments of deployment device 30 may contain modified channel locations in head housing 68. These locations may be needed to place flexible tubes 28 and 29 in different locations, particularly at different sphincter sites as in some embodiments.

Figure 12:
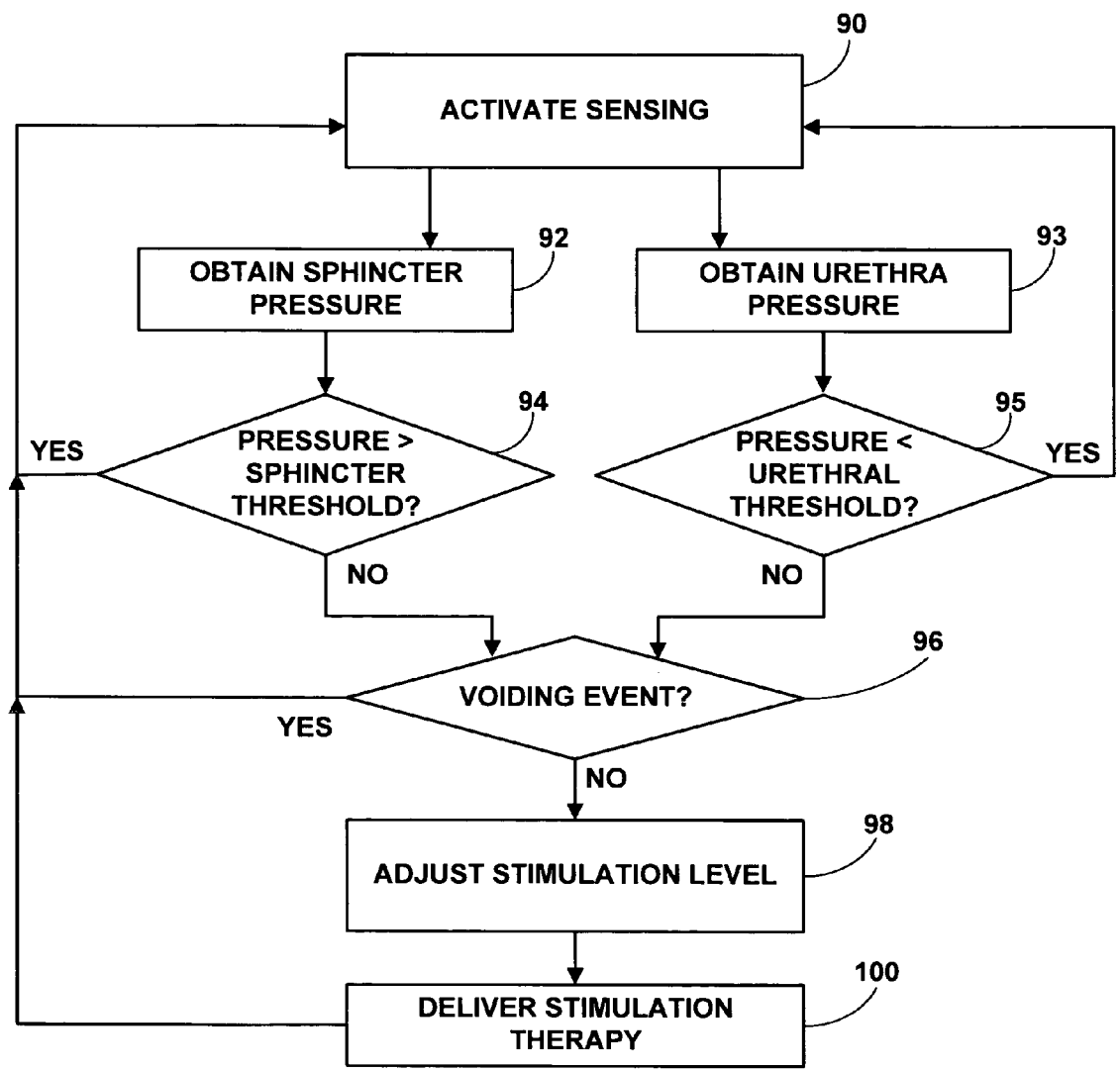
FIG. 12 is a flow chart illustrating a technique for delivery of stimulation therapy based on closed loop feedback from an implantable pressure sensor.

FIG. 12 is a flow chart illustrating a technique for delivery of stimulation therapy based on closed loop feedback from an implantable pressure sensor 12. In the example of FIG. 11, implantable stimulator 14 makes use of information from implantable pressure sensor 12 and external programmer 16. Implantable stimulator 14 communicates with implantable pressure sensor 12 to activate sensing (90). Pressure sensor 12 acquires a sphincter pressure measurement from flexible tube 28 (92) and a urethra pressure measurement (93) from flexible tube 29. The pressure information may be delivered to implantable stimulator 14 or external programmer 16 by wireless telemetry.

Upon receiving the sphincter and urethra pressure data, implantable stimulator 14 compares the respective pressure levels to applicable threshold levels (94 and 95). The urinary sphincter pressure level may be a level above which urinary sphincter 22 exhibits adequate closing pressure. The urethral pressure level may be a level above which urethra 20 exhibits excessive fluid pressure, indicating urine voiding. If measured urinary sphincter pressure is higher than the applicable threshold and measured urethral pressure is below the applicable threshold, there is no indication of a voiding episode, and the process returns to the next sensing activation (90).

If sphincter pressure is below the applicable threshold or urethral pressure is above the applicable threshold, implantable stimulator 14 determines whether the patient has elected to commence a voluntary voiding event (96). If so, the process returns to the next sensing activation (90). If the patient has not elected to commence a voluntary voiding event (96), however, deviation of the sphincter pressure below the applicable threshold or deviation of urethral pressure above the applicable threshold may indicate an involuntary voiding event, i.e., involuntary leakage. In this case, in an effort to stop or avoid involuntary leakage, implantable stimulator 14 adjusts the level of stimulation (98) and delivers the adjusted stimulation to the patient (100).

The process outlined in FIG. 12 takes advantage of both urinary sphincter and urethral pressure measurements to determine whether stimulation should be adjusted. If patient 18 has signaled a voiding event, e.g., by depression of a button on external programmer 16, stimulation adjustment is skipped and the process begins again. In the case of involuntary leakage, however, sphincter 22 is not providing adequate closing pressure and needs to be stimulated more aggressively. In the example of FIG. 12, urinary sphincter pressure and urethral pressure provide alternative, redundant modes for identification of involuntary voiding episodes. If either pressure level deviates relative to an applicable threshold, more aggressive stimulation is applied to prevent leakage.

In some embodiments, pressure sensor 12 may be used exclusively for monitoring sphincter and urethra pressure without providing feedback to a stimulator for interventional therapy. Pressure may be measured every few seconds, minutes, hours, or at the request of external programmer 16. These embodiments may be used for disease diagnosis or condition monitoring and may enable a patient to avoid frequent clinic visits and multiple uncomfortable procedures. In some embodiments, the pressure measurements may form part of an automated voiding diary that records voluntary voiding events, involuntary voiding events, and urinary sphincter and urethral pressure levels prior to, contemporaneous with, of after such an event. In some embodiments, the pressure measurements may form part of an automated voiding diary that records voluntary voiding events, involuntary voiding events, and urinary sphincter and urethral pressure levels prior to, contemporaneous with, of after such an event.

Although the invention may be especially applicable to sensing urinary sphincter and urethral pressure, the invention alternatively may be applied more generally to other sphincters within the patient, such as the lower esophageal sphincter (LES) or pyloric sphincter and adjacent structures. In addition, in those instances, the invention may be adapted to support electrical stimulation of other body organs, such as the stomach or intestines, e.g., for treatment of obesity or gastric mobility disorders. Not only may stimulation of certain nerves allow for the proper closure of a sphincter, but nerve stimulation may be able to modify stomach contractions or intestinal contractions based upon pressure measurements at those sites. Pressure feedback from the implantable pressure sensor may provide the most effective therapy for some patients, e.g., in the form of biofeedback that aids the patient in self-regulating bladder control.

Various embodiments of the described invention may include processors that are realized by microprocessors, Application-Specific Integrated Circuits (ASIC), Field-Programmable Gate Array (FPGA), or other equivalent integrated or discrete logic circuitry. The processor may also utilize several different types of storage methods to hold computer-readable instructions for the device operation and data storage. These memory or storage media may include a type of hard disk, random access memory (RAM), or flash memory, e.g. Compact Flash or Smart Media. Each storage option may be chosen depending on the embodiment of the invention. While the implantable stimulator and implantable pressure sensor may contain permanent memory, the patient or clinician programmer may contain a more portable removable memory type to enable easy data transfer for offline data analysis.

Many embodiments of the invention have been described. Various modifications may be made without departing from the scope of the claims. For example, although the invention has been generally described in conjunction with implantable neurostimulation devices, a flexible tube sensor may also be used with other implantable medical devices, such as electrical muscle stimulation devices, functional electrical stimulation (FES) devices, and implantable drug delivery devices, each of which may be configured to treat incontinence or other conditions or disorders. These and other embodiments are within the scope of the following claims.

The invention claimed is:

1. An implantable pressure sensor comprising:
 a sensor housing;
 a first flexible tube extending from the housing;
 a second flexible tube extending from the housing; and
 a sensing device that senses a fluid pressure within the first flexible tube indicative of a urinary sphincter pressure level outside of the first flexible tube when the first flexible tube is positioned adjacent a urinary sphincter of a patient, and senses a fluid pressure within the second flexible tube indicative of a urethral pressure level outside of the second flexible tube when the second flexible tube is positioned within a urethra of the patient,
 wherein each of the first flexible tube and the second flexible tube includes a closed distal end and an open proximal end in communication with the sensing device, and wherein a proximal portion of the second flexible tube is disposed within the first flexible tube, and a distal portion of the second flexible tube extends beyond a distal portion of the first flexible tube such that the distal portion of the second flexible tube is positioned within the urethra when the first flexible tube is positioned adjacent to the urinary sphincter.

2. The sensor of claim 1, wherein the second flexible tube is longer than the first flexible tube.

3. The sensor of claim 1, wherein the second flexible tube is disposed substantially concentrically within the first flexible tube.

4. The sensor of claim 1, further comprising a substantially rigid interface tube that separates an outer surface of the second flexible tube from an inner surface of the first flexible tube.

5. The sensor of claim 4, wherein the first flexible tube comprises a material, the second flexible tube comprise the same material, and the rigid interface tube comprises the same material with a greater density than the first flexible tube and the second flexible tube.

6. The sensor of claim 4, wherein the rigid interface tube is configured to substantially prevent pressure exerted on the first flexible tube from affecting the pressure within the second flexible tube.

7. The sensor of claim 1, wherein the sensing device includes a first sensing element that senses the fluid pressure within the first flexible tube, and a second sensing element that senses the fluid pressure within the second flexible tube.

8. The sensor of claim 1, wherein the sensing device includes a strain gauge sensor that generates an electrical signal indicative of fluid pressure within at least one of the first and second flexible tubes.

9. The sensor of claim 1, further comprising a wireless telemetry interface that transmits information based on the sensed fluid pressure.

10. The sensor of claim 1, wherein the sensor housing includes a fixation mechanism to mount the sensor housing within a bladder of a patient.

11. The sensor of claim 1, further comprising a memory that stores information based on the sensed pressures.

12. The sensor of claim 1, wherein the first flexible tube has an outer diameter sized less than an inner diameter of the urethra.

13. The sensor of claim 1, wherein the first flexible tube has a substantially circular cross-section.

14. The sensor of claim 1, wherein the distal portion of the second flexible tube extends approximately 1 to 3 centimeters beyond the distal portion of the first flexible tube.

15. A system comprising:
an implantable pressure sensor comprising:
a sensor housing,
a first flexible tube extending from the housing,
a second flexible tube extending from the housing, and
a sensing device that senses a fluid pressure within the first flexible tube indicative of a urinary sphincter pressure level outside of the first flexible tube when the first flexible tube is positioned adjacent a urinary sphincter of a patient, and senses a fluid pressure within the second flexible tube outside of the second flexible tube indicative of a urethral pressure level when the second flexible tube is positioned within a urethra of the patient,
wherein each of the first flexible tube and the second flexible tube includes a closed distal end and an open proximal end in communication with the sensing device, and
wherein a proximal portion of the second flexible tube is disposed within the first flexible tube, and a distal portion of the second flexible tube extends beyond a distal portion of the first flexible tube such that the distal portion of the second flexible tube is positioned within the urethra when the first flexible tube is positioned adjacent to the urinary sphincter; and
an implantable stimulator that delivers electrical stimulation to the patient based on the sensed pressures.

16. The system of claim 15, wherein the second flexible tube is longer than the first flexible tube.

17. The system of claim 15, wherein the second flexible tube is disposed substantially concentrically within the first flexible tube.

18. The system of claim 15, wherein the sensing device includes a first sensing element that senses the fluid pressure within the first flexible tube, and a second sensing element that senses the fluid pressure within the second flexible tube.

19. The system of claim 15, further comprising a wireless telemetry interface that transmits information based on the sensed fluid pressure to the implantable stimulator.

20. The system of claim 19 wherein the implantable stimulator adjusts one or more stimulation parameters of the electrical stimulation based on the transmitted information.

21. The system of claim 19, further comprising an external programmer to adjust stimulation parameters associated with the electrical stimulation delivered by the implantable stimulator, wherein the telemetry interface transmits the information to the external programmer.

22. The system of claim 19, wherein the implantable stimulator is configured to deliver electrical stimulation to the patient to alleviate urinary incontinence.

23. A method comprising:
sensing via a sensing device a first pressure level exerted by a urinary sphincter within a patient based on a pressure of fluid within a first flexible tube placed proximate to the urinary sphincter; and
sensing via the sensing device a second pressure level exerted within a urethra of the patient based on a pressure of fluid within a second flexible tube placed within the urethra below the urinary sphincter,
wherein each of the first flexible tube and the second flexible tube includes a closed distal end and an open proximal end in communication with the sensing device, and
wherein a proximal portion of the second flexible tube is disposed within the first flexible tube, and a distal portion of the second flexible tube extends beyond a distal portion of the first flexible tube such that the distal portion of the second flexible tube is positioned within the urethra when the first flexible tube is positioned adjacent to the urinary sphincter.

24. The method of claim 23, further comprising delivering electrical stimulation to the patient based on the sensed pressure levels.

25. The method of claim 24, wherein the electrical stimulation is configured to alleviate urinary incontinence.

26. The method of claim 23, further comprising transmitting information based on the sensed pressure level to an implantable stimulator via wireless telemetry, and adjusting electrical stimulation delivered to the patient based on the transmitted information.

27. The method of claim 23, further comprising transmitting information based on the sensed pressure level to an external programmer via wireless telemetry, wherein the external programmer adjusts stimulation delivered by an implantable stimulator based on the transmitted information.

28. The method of claim 23, wherein the first and second flexible tubes extend from a sensor housing, the method further comprising:

mounting the sensor housing within a bladder of the patient;

positioning the first flexible tube to extend downward from the bladder and through the urinary sphincter; and positioning the second flexible tube to extend downward from the bladder and into the urethra below the urinary sphincter.

* * * * *